(12) United States Patent
Fujimoto et al.

(10) Patent No.: US 8,715,271 B2
(45) Date of Patent: May 6, 2014

(54) LINEAR BODY DRIVE DEVICE

(75) Inventors: Hideo Fujimoto, Nagoya (JP); Akihito Sano, Nagoya (JP); Yoshitaka Nagano, Iwata (JP)

(73) Assignees: National University Corporation Nagoya Institute of Technology, Aichi (JP); NTN Corporation, Osaka (JP)

( * ) Notice: Subject to any disclaimer, the term of this patent is extended or adjusted under 35 U.S.C. 154(b) by 1244 days.

(21) Appl. No.: 12/595,363

(22) PCT Filed: Mar. 21, 2008

(86) PCT No.: PCT/JP2008/055268
§ 371 (c)(1), (2), (4) Date: Oct. 9, 2009

(87) PCT Pub. No.: WO2008/126656
PCT Pub. Date: Oct. 23, 2008

(65) Prior Publication Data
US 2010/0057099 A1 Mar. 4, 2010

(30) Foreign Application Priority Data
Apr. 10, 2007 (JP) ................................. 2007-102962

(51) Int. Cl.
*A61B 1/01* (2006.01)
*G01L 1/00* (2006.01)

(52) U.S. Cl.
USPC ........ 606/1; 600/114; 604/95.01; 73/862.642

(58) Field of Classification Search
USPC .................. 606/1; 600/114, 145; 73/849, 73/862–862.382
See application file for complete search history.

(56) References Cited

U.S. PATENT DOCUMENTS 6,096,004 A * 8/2000 Meglan et al. ............. 604/95.01
6,272,371 B1 8/2001 Shlomo
(Continued)

FOREIGN PATENT DOCUMENTS

JP 8-224246 9/1996
JP 9-149939 6/1997
(Continued)

OTHER PUBLICATIONS

Japanese Office Action, and English translation thereof, issued in Japanese Patent Application No. 2007-102962 dated Mar. 27, 2012.
(Continued)

*Primary Examiner* — Gary Jackson
*Assistant Examiner* — Michael M Kim
(74) *Attorney, Agent, or Firm* — McDermott Will & Emery LLP (57) ABSTRACT

A linear body drive device capable of safely and reliably operating a linear body is provided. A linear body insertion device includes a drive portion, an operation portion, a sensor portion and a processing portion serving as a measurement portion, and an output portion serving as a notification portion. The drive portion drives a linear body having flexibility. The operation portion includes an input member (an operation lever) operated by an operator for controlling performance of the drive portion. The sensor portion included in the measurement portion detects compressive force in a direction of longitudinal axis applied to the linear body, based on a degree of bending of the linear body driven by the drive portion. The output portion provides notification of data of compressive force detected by the measurement portion.

8 Claims, 9 Drawing Sheets

(56) References Cited

U.S. PATENT DOCUMENTS

| | | | |
|---|---|---|---|
| 6,375,471 | B1 | 4/2002 | Wendlandt et al. |
| 6,981,945 | B1 | 1/2006 | Sarvazyan et al. |
| 2006/0161043 | A1* | 7/2006 | Neumann et al. ............ 600/114 |

FOREIGN PATENT DOCUMENTS

| | | |
|---|---|---|
| JP | 2000-042116 | 2/2000 |
| JP | 2000-42117 | 2/2000 |
| JP | 2000-508224 | 7/2000 |
| JP | 2000-514320 | 10/2000 |
| JP | 2004-239667 | 8/2004 |
| WO | WO 97/44089 | 11/1997 |
| WO | WO 98/29033 | 7/1998 |
| WO | WO 2007/111182 A1 | 10/2007 |

OTHER PUBLICATIONS

Lazeroms, M., et al., "Optical Fibre Force Sensor for Minimal-Invasive-Surgery Grasping Instruments", 18th Annual International Conference of the IEEE Engineering in Medicine and Biology Society, Amsterdam, 1996 1.5.2: Microsurgical and Robotic Interventions II, pp. 234-235, IEEE.

Appleyard, M.N., et al., "The measurement of forces exerted during colonoscopy", Gastrointestinal Endoscopy, vol. 52 No. 2, 2000, Elsevier.

Supplementary European Search Report, issued in European Patent Application No. EP 08 72 2632, dated Jan. 31, 2011.

* cited by examiner

FIG.18

LINEAR BODY DRIVE DEVICE

RELATED APPLICATIONS

This application is the U.S. National Phase under 35 U.S.C. §371 of International Application No. PCT/JP2008/055268, filed on Mar. 21, 2008, which in turn claims the benefit of Japanese Application No. 2007-102962, filed on Apr. 10, 2007, the disclosures of which Applications are incorporated by reference herein.

TECHNICAL FIELD

The present invention relates to a linear body drive device, and more particularly to a device for driving a flexible linear body such as a guide wire inserted in a body.

BACKGROUND ART

A linear body having flexibility has been put into practical use, for example, as a linear medical appliance inserted in a vessel in a body. Specifically, a guide wire or a catheter inserted in a vessel in a body such as a blood vessel, a ureter, a bronchus, an alimentary canal, or a lymph vessel, a wire having an embolic coil attached at a tip end for embolizing an aneurysm, or the like has been known.

Applications of such a linear body include, for example, a surgical operation for embolizing a cerebral aneurysm with a platinum coil or the like in order to avoid rupture of the cerebral aneurysm, which is a cause of subarachnoid hemorrhage. In this case, a wire provided with an embolic coil at a tip end, that can be detached by applying electricity or water pressure, is used to fill the cerebral aneurysm with the coil. In order to fill the aneurysm with the coil, a catheter for guiding a wire provided with the coil to the cerebral aneurysm should be brought to the cerebral aneurysm.

Here, as the catheter is made of a soft material, the catheter cannot reach the cerebral aneurysm by itself. Accordingly, the catheter is guided to the cerebral aneurysm by using an extremely thin wire called a guide wire. Specifically, the guide wire representing a linear body is inserted in a hole in the center of the catheter, and in this state, the catheter in which the guide wire has been inserted is inserted in a human body. Then, the catheter is guided to the cerebral aneurysm by operating the guide wire from the outside of the human body. When the catheter is guided to the cerebral aneurysm by using the guide wire, the guide wire is subsequently pulled out of the catheter. Thereafter, the wire provided with the coil at the tip end is inserted in the hole of the catheter.

In a surgical operation for embolizing the cerebral aneurysm, in order to densely fill the cerebral aneurysm of which blood vessel wall has become thin with a plurality of coils, the wire provided with the coil should be operated with extreme care. On the other hand, an operation of the wire requires skills as it is performed from the outside of the human body. As such, though a surgical operation for embolization above is advantageous in that less burden is imposed on a human body than in a conventional surgical operation, the operation of the wire provided with the coil is highly difficult and the surgical operation has been difficult.

In order to solve such a problem, for example, a system using main and sub actuators is available as shown in Japanese Patent Laying-Open No. 2000-42116 (Patent Document 1). According to this system, in order for an operator to delicately operate a linear body, movement of a main actuator operated by the operator is carried out on a different scale by a sub actuator directly driving the wire.

Patent Document 1: Japanese Patent Laying-Open No. 2000-42116

DISCLOSURE OF THE INVENTION

Problems to be Solved by the Invention

The conventional system described above, however, has suffered the following problem. Specifically, in the system above, a sensor for sensing movement in an axial direction of the linear body or rotation around the axis is attached to the actuator. Here, compressive force applied to the linear body cannot accurately be detected only based on an amount of travel of the linear body sensed by the sensor. Consequently, it has been difficult to sufficiently carry out control (feedback control or the like) or an operation, in consideration of a value of compressive force applied to the linear body.

For example, when the linear body is moved by rotation of a roller or the like, means for calculating compressive force applied to the linear body based on torque of a motor for rotating the roller or the like is also possible. Even with such means, however, it is difficult to accurately calculate compressive force applied to the linear body for the following reasons. Specifically, in the surgical operation for embolizing an aneurysm described above, the linear body should be inserted slowly so as not to cause rupture of the aneurysm. Therefore, a decelerator great in a reduction ratio is attached between the motor and the roller. As the decelerator is interposed, when compressive force is determined based on torque of the motor, slight fluctuation in load due to variation of compressive force applied to the linear body appears to be smaller by the reduction ratio of the decelerator. Therefore, it is difficult to accurately measure a value of compressive force applied to the linear body based on determination of torque of the motor.

The present invention was made to solve the above-described problems, and an object of the present invention is to provide a linear body drive device capable of safely and reliably operating the linear body by accurately measuring compressive force applied to the linear body.

Means for Solving the Problems

A linear body drive device according to the present invention includes a drive portion, an operation portion, a measurement portion, and a notification portion. The drive portion drives a linear body having flexibility. The operation portion includes an input member operated by an operator for controlling performance of the drive portion. The measurement portion detects compressive force in a direction of longitudinal axis applied to the linear body, based on a degree of bending of the linear body driven by the drive portion. The notification portion provides notification of data of the compressive force detected by the measurement portion.

The compressive force in the direction of longitudinal axis applied to the linear body can thus accurately be detected based on the degree of bending of the linear body, so that the operator can operate the operation portion based on the data of the compressive force provided by the notification portion. Consequently, the operator can safely and reliably operate the linear body.

In the linear body drive device above, the measurement portion may include a main body, a sensor, and a conversion portion. In the main body, a through hole through which the linear body passes may be formed. When the compressive force is applied to the linear body, the linear body may be bent in a prescribed direction within the through hole. The sensor may detect the degree of bending. The conversion portion converts the detected degree of bending into the compressive force applied to the linear body.

Here, when compressive force in the direction of longitudinal axis is applied to the linear body as a result of contact of a tip end of the linear body with an obstacle, the measurement portion can detect the degree of bending of the linear body with the sensor. Then, the detected degree of bending of the linear body can be converted into compressive force in the direction of longitudinal axis applied to the linear body, for example, based on predetermined correlation between the degree of bending of the linear body and the compressive force applied to the linear body, so that presence of the obstacle in a direction of travel of the linear body can be sensed based on increase in the compressive force. Here, the measurement portion is arranged in the linear body drive device located outside a vessel in which the linear body is to be inserted (for example, an output side of the drive portion and outside the human body), and it can measure compressive force in the direction of longitudinal axis applied to the linear body.

In addition, for example, compressive force applied to the linear body can quantitatively be measured also in regard to an extremely thin linear body where it is difficult to provide a pressure sensor at the tip end. Moreover, as the linear body drive device according to the present invention is not much restricted in terms of a material or the like for the linear body to be used, it is applicable to linear bodies of various shapes or materials. Consequently, the linear body as used so far can be used with the linear body drive device according to the present invention without modification, which leads to cost effectiveness.

In the linear body drive device above, the drive portion may include a pair of rollers sandwiching the linear body, and a drive member. The drive member may rotatably drive at least one of the pair of rollers. Here, the drive portion can be implemented by relatively simple devices of the drive member and the rollers as combined.

In the linear body drive device above, the operation portion and the drive portion may mechanically be separated from each other. The linear body drive device above may further include a connection member for electrically connecting the separated operation portion and drive portion to each other. Here, for example, when the linear body drive device is applied for driving a guide wire or the like of a medical catheter, a patient in which the catheter is to be inserted is under X-ray fluoroscopy. Therefore, in order to minimize exposure of the operator of the drive device to X-rays, the operator preferably operates the drive device at a position as distant as possible from the patient. Accordingly, if the operation portion and the drive portion can be separated from each other as above, only the operation portion can be arranged at a position distant from the drive portion (which is provided around the patient), so that the operator can operate the drive device at a position distant from the patient.

In the linear body drive device above, a connection member may be a wire for electrically connecting the drive portion and the operation portion to each other, an optical fiber for transmitting an optical signal, or a transmitter and a receiver provided in each of the drive portion and the operation portion, capable of transmitting and receiving a signal through an electromagnetic wave (light, infrared, or other electromagnetic waves) between the drive portion and the operation portion.

In the linear body drive device above, the operation portion may have at least any one of a lever, a pedal, and a dial, as the input member. Here, the operation portion can be implemented as a relatively simple structure.

In the linear body drive device above, the notification portion may include at least any one of a visualizing instrument for displaying data and an auralizing instrument for converting the data into voice and sound for output. Here, the visualizing instrument and the auralizing instrument can quantify and display kinesthetic sense of the operator. In addition, such data can also be recorded. Therefore, manipulation of a skilled operator can quantitatively be transferred to a less experienced operator. Moreover, the operator can reliably recognize the time when compressive force applied to the linear body is equal to or greater than a predetermined threshold value.

In the linear body drive device above, the measurement portion may output a signal in accordance with the data of the compressive force to the operation portion. The operation portion may include a feedback output member for varying an operation resistance of the input member in accordance with the signal. Here, the compressive force applied to the linear body can be transmitted to the operator as tactile sense, depending on magnitude of resistance in operation of the input member of the operation portion by the operator (magnitude of force necessary for moving the input member).

In the linear body drive device above, a linear body for medical use may be employed as the linear body. Here, as the linear body drive device according to the present invention can be used in a surgical operation or the like using the linear body for medical use, the linear body can safely and reliably be operated while the data of compressive force applied to the linear body is quantitatively grasped. Therefore, safety and accuracy of the surgical operation using the linear body can be improved.

The linear body drive device above may be provided in a medical simulator simulating a human body. Here, manipulation of a skilled operator can be quantified and quantitative transfer of manipulation to a less experienced operator can be promoted. Therefore, manipulation of the less experienced operator can quickly be improved.

Effects of the Invention

As compressive force in the direction of longitudinal axis applied to the linear body can accurately be detected based on the degree of bending of the linear body, the operator can operate the operation portion based on the data of the compressive force provided by the notification portion. Consequently, the linear body can safely and reliably be operated.

DESCRIPTION OF THE REFERENCE SIGNS 1 linear body; 2 measurement device main body; 3 through hole; 4 input port; 6 output port; 7, 8 restraint portion; 10 space; 11 line sensor; 12 linear light source; 13 linear light receiver; 14 illumination control circuit; 15 conversion circuit; 16 selector; 17 tactile sense feedback portion; 18 light source; 19 light receiver; 24, 48 operator; 25 human body; 26, 27 visualizing instrument; 28 auralizing instrument; 29 speaker; 30 upper housing; 31 lower housing; 32 hinge; 33 locking portion; 34, 37 roller; 35, 38 rubber; 36, 47 motor; 39, 45 arrow; 40 lever; 41 housing; 42 potentiometer; 43 rotation shaft; 44 return spring; 46 decelerator; 49 connection wire; 50 CPU; 51 A/D converter; 52 D/A converter; 53 display circuit; 61 simulator; 62 simulated perspective image; 63 cable; 66 catheter; 71 strain sensor; 72 elastic body; 73 amplifier circuit; 80 illumination control circuit; 110 sensor portion; 120 processing portion; 130 drive portion; 140 operation portion; and 150 output portion.

BEST MODES FOR CARRYING OUT THE INVENTION

An embodiment of the present invention will be described hereinafter with reference to the drawings. In the drawings below, the same or corresponding elements have the same reference characters allotted and detailed description thereof will not be repeated.

A linear body insertion device according to the present invention will be described with reference to FIGS. 1 and 2.

Figure 1:
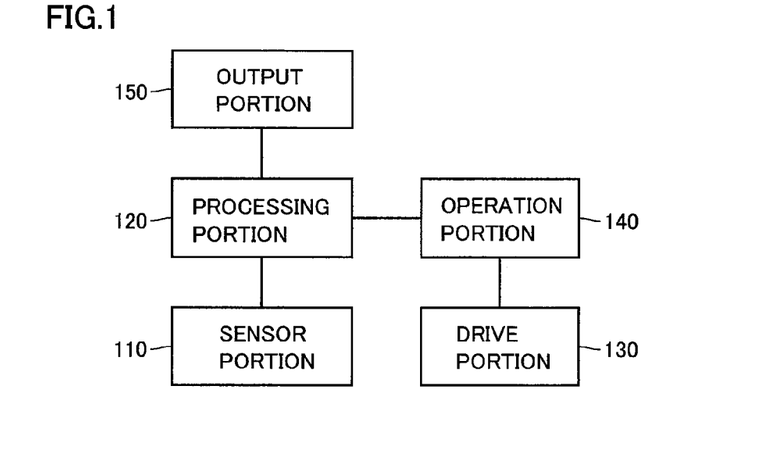
FIG. 1 is a block diagram showing an overall configuration of a linear body insertion device according to the present invention.

As shown in FIG. 1, a linear body insertion device representing an exemplary linear body drive device according to the present invention includes a sensor portion 110, a drive portion 130, a processing portion 120, an operation portion 140, and an output portion 150. As shown in FIG. 2, sensor portion 110 is a detection device connected to an output side of drive portion 130, for detecting compressive force applied to linear body 1 inserted to pass through sensor portion 110 via drive portion 130. Drive portion 130 serves to move linear body 1 forward or backward by transmitting motive force for moving linear body 1 forward and backward to linear body 1.

Figure 2:
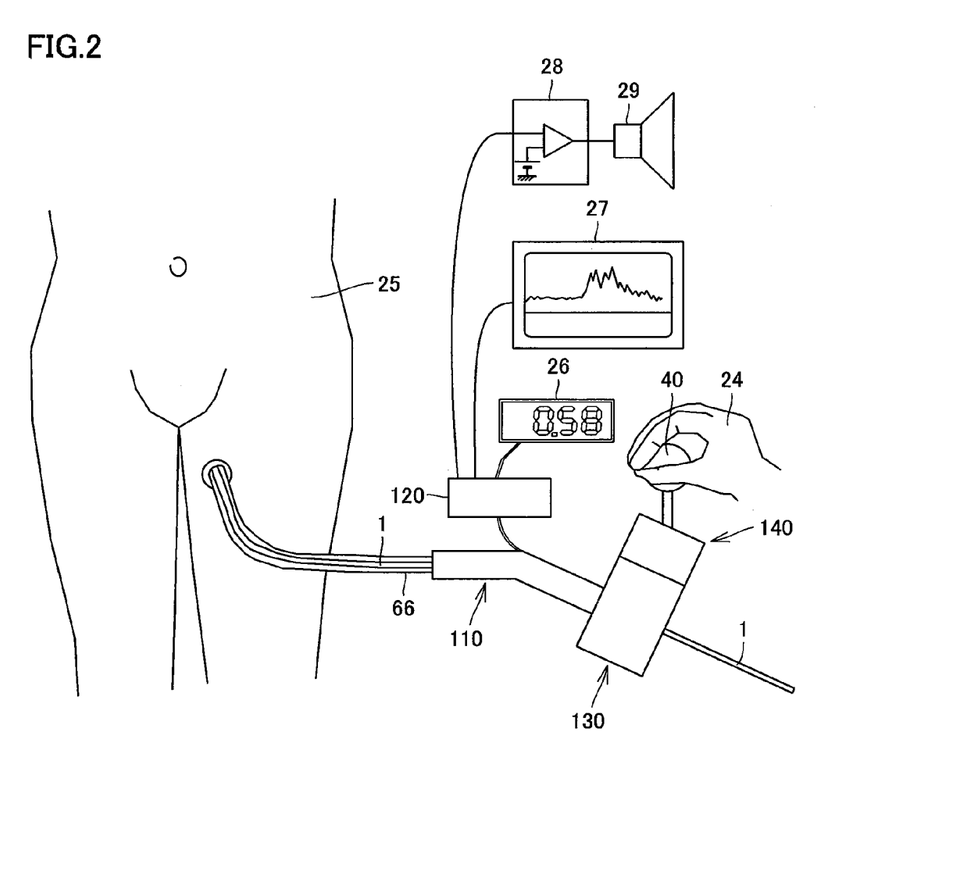
FIG. 2 is an overall schematic diagram showing a state of use of the linear body insertion device according to the present invention shown in FIG. 1.

As shown in FIG. 2, operation portion 140 is provided with an operation lever 40 serving as an input member, and performance of drive portion 130 is controlled by the operation of operation lever 40 by an operator 24. Processing portion 120 receives an output from sensor portion 110 and outputs data of compressive force in the direction of longitudinal axis applied to linear body 1 by processing the output. Output portion 150 is implemented by a visualizing instrument 26, 27 or an auralizing instrument 28 and a speaker 29 connected to the auralizing instrument as shown in FIG. 2, for showing an output from processing portion 120 to the operator. A detailed structure of each member above will be described later.

The linear body insertion device shown in FIGS. 1 and 2 employs, for example, a linear body such as a wire for medical use. Namely, for example, a wire having a coil for embolizing a cerebral aneurysm attached at the tip end is applicable as linear body 1. Such a linear body 1 is inserted in a human body 25 together with a catheter 66. According to the linear body insertion device shown in FIGS. 1 and 2, in thus inserting linear body 1 into the human body, sensor portion 110 detects force (compressive force) applied to linear body 1. Then, the output from this sensor portion 110 is presented to the operator by means of output portion 150 through processing portion 120. Operator 24 can perform such an operation as moving forward or backward linear body 1, by operating operation lever 40 or the like, based on information of an image of the linear body in the human body in an X-ray fluoroscopic image of the human body in which linear body 1 has been inserted and compressive force applied to the linear body shown on output portion 150 described above.

A specific structure of each member of the linear body insertion device above will now be described.

The sensor portion of the linear body insertion device according to the present invention will be described with reference to FIGS. 3 and 4.

Figure 3:
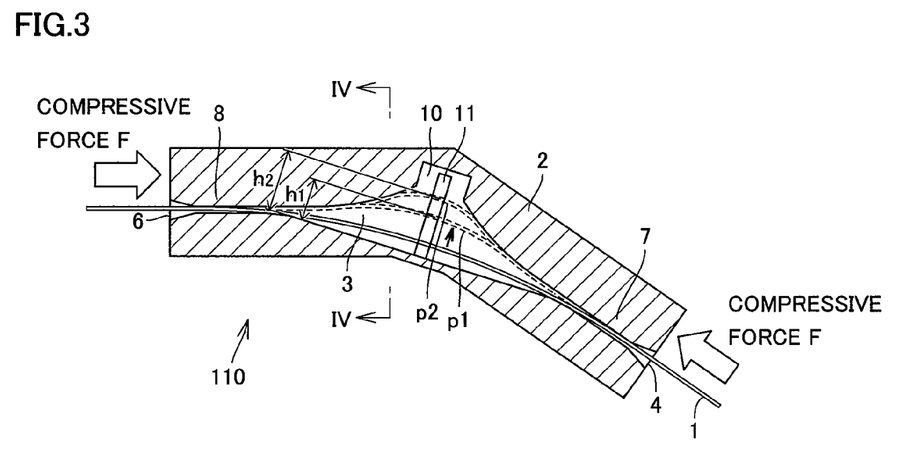
FIG. 3 is a cross-sectional schematic diagram of a sensor portion of the linear body insertion device shown in FIGS. 1 and 2.
Figure 4:
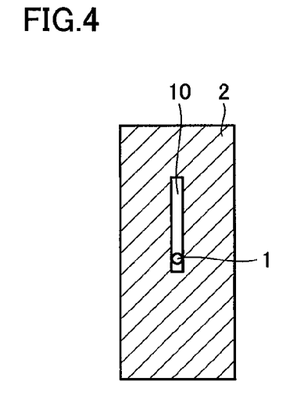
FIG. 4 is a cross-sectional schematic diagram along the line IV-IV in FIG. 3.

As shown in FIGS. 3 and 4, sensor portion 110 includes a measurement device main body 2 in which a through hole in which linear body 1 can be inserted is formed and a line sensor 11 for detecting a state of bending of linear body 1 within the through hole. Specifically, in measurement device main body 2, an input port 4 of a through hole 3 is formed in one certain side surface, and an output port 6 of through hole 3 is formed in another side surface. Through hole 3 is formed such that it bends within measurement device main body 2 from input port 4 toward output port 6. In addition, in through hole 3, restraint portions 7 and 8 for restraining linear body 1 are formed on inner sides of input port 4 and output port 6, respectively. A space 10 where a width of through hole 3 is great is formed between restraint portions 7 and 8, in a bending portion of through hole 3. Line sensor 11 is provided at a substantially central portion of space 10 where the width of through hole 3 is great such that it intersects a direction of extension of through hole 3.

As shown in FIG. 4, space 10 in through hole 3 is sufficiently great in its width with respect to a diameter of linear body 1, whereas it has a height substantially equivalent to the diameter of linear body 1 (that is, a height with a slight margin to such an extent to permit insertion of linear body 1). Therefore, when compressive force F is applied to linear body 1 as shown in FIG. 3, linear body 1 is bent within space 10. Heights h1 and h2 of a bent portion when linear body 1 is bent are determined by magnitude of compressive force F. Within space 10, line sensor 11 detects bending heights h1 and h2 of linear body 1 bent in accordance with compressive force F. Data of bending heights h1 and h2 is output to processing portion 120 which will be described later, where compressive force F is calculated based on bending heights h1 and h2. Here, bending heights h1 and h2 of linear body 1 refer to a distance from one sidewall of space 10 (an inner sidewall in the bending portion of through hole 3) to linear body 1.

As shown in FIG. 3, through hole 3 is in a bending state such that a direction of extension of through hole 3 at input port 4 and a direction of extension of through hole 3 at output port 6 intersect with each other within space 10. In addition, as shown in FIG. 4, regarding the width and the height of space 10, the width of space 10 is sufficiently great in the direction of bending of linear body 1, while the height of space 10 is sufficiently small to such an extent to restrict movement of linear body 1 (for example, a height from 105% to 120% of the diameter of linear body 1). Therefore, magnitude of compressive force F applied to linear body 1 substantially accurately corresponds to a degree of bending of linear body 1 within space 10 in the direction of width of space 10. Accordingly, by finding correspondence between the degree of bending of linear body 1 (bending height) and compressive force F in advance, compressive force F can be found based on the degree of bending.

A structure of operation portion 140 will now be described. The structure of the operation portion of the linear body insertion device according to the present invention will be described with reference to FIGS. 5 and 6.

Figure 5:
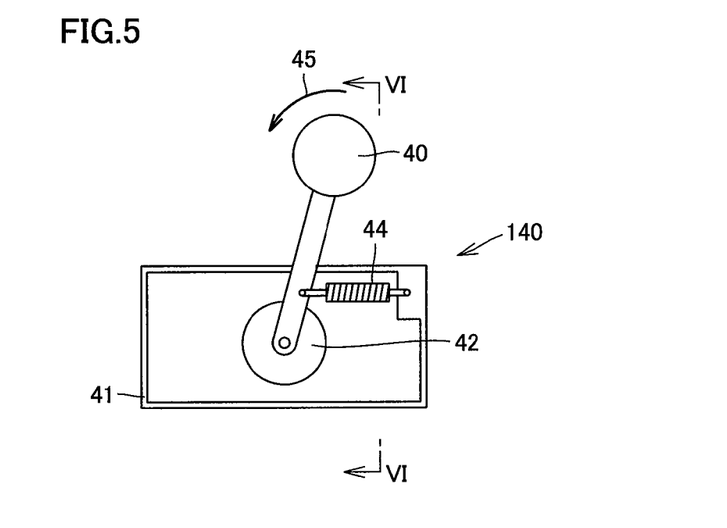
FIG. 5 is a cross-sectional schematic diagram showing a structure of an operation portion.
Figure 6:
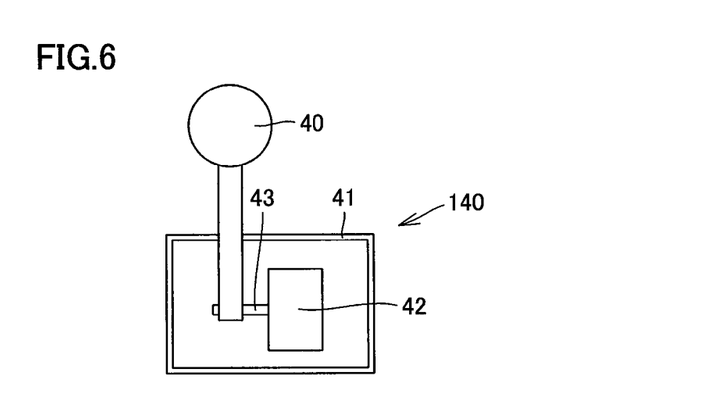
FIG. 6 is a cross-sectional schematic diagram along the line VI-VI in FIG. 5.

As shown in FIGS. 5 and 6, operation portion 140 includes a housing 41, a potentiometer 42 arranged inside housing 41, operation lever 40 connected to potentiometer 42, and a return spring 44 for returning operation lever 40 to an initial position. Though housing 41 has a cubic shape, housing 41 may have another shape. Operation lever 40 has one end connected to a rotation shaft 43 of potentiometer 42. In operation lever 40, a ball-shaped portion serving as a grip portion for facilitating grip of operation lever 40 by the operator is formed at the other end, which is an end portion located opposite to one end. The ball-shaped portion of operation lever 40 is projecting outward from housing 41. In addition, a connection portion to which one end of return spring 44 is connected is formed at an intermediate portion of operation lever 40 between one end and the other end described above. Return spring 44 has one end connected to the connection portion and has the other end connected and fixed to an inner wall of housing 41.

Structured as such, when the operator operates operation lever 40 in a direction shown with an arrow 45, an angle of rotation of operation lever 40 in the direction of arrow 45 can be detected by potentiometer 42. When the operator stops operating operation lever 40 (that is, the operator releases his/her hand from operation lever 40), operation lever 40 returns to the initial position as shown in FIG. 5, owing to force applied by return spring 44. An output of potentiometer 42 is transmitted to drive portion 130 which will be described later, and used for controlling an output of a drive source such as a motor which implements drive portion 130.

A variation of the operation portion of the linear body insertion device according to the present invention will be described with reference to FIG. 7. It is noted that FIG. 7 corresponds to FIG. 6.

Figure 7:
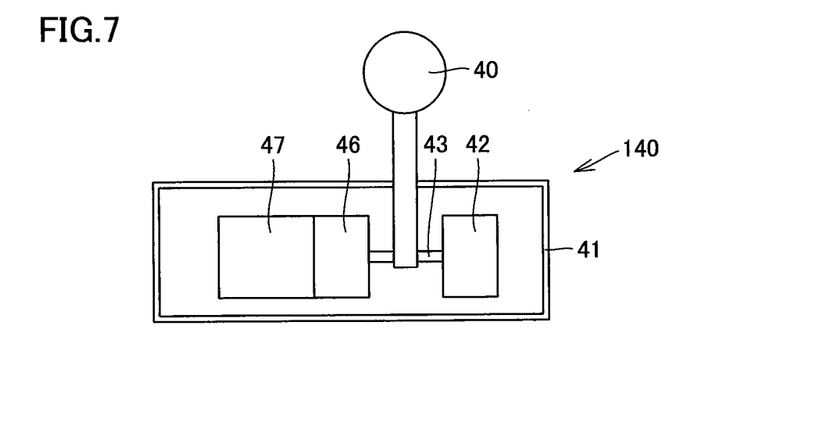
FIG. 7 is a cross-sectional schematic diagram showing a variation of the operation portion shown in FIGS. 5 and 6.

Though operation portion 140 shown in FIG. 7 has a structure basically similar to that of the operation portion shown in FIGS. 5 and 6, it is different in that a motor 47 serving as a feedback output member is connected, with a decelerator 46 being interposed on a side of rotation shaft 43 to which operation lever 40 is connected, opposite to where potentiometer 42 is connected. According to such a structure, in accordance with compressive force F applied to linear body 1 detected by sensor portion 110, torque can be transmitted to operation lever 40 through motor 47 and decelerator 46, in a direction opposite to the direction shown with arrow 45 shown in FIG. 5. In other words, force required for operating operation lever 40 can be increased or decreased, in accordance with compressive force applied to linear body 1 in sensor portion 110. Consequently, the operator can sense compressive force not only based on the data of compressive force from output portion 150 and positional information of the wire in the X-ray fluoroscopic image but also on magnitude of force required for operating operation lever 40.

Feedback control in the linear body insertion device having operation portion 140 shown in FIG. 7 will be described with reference to FIG. 8.

Figure 8:
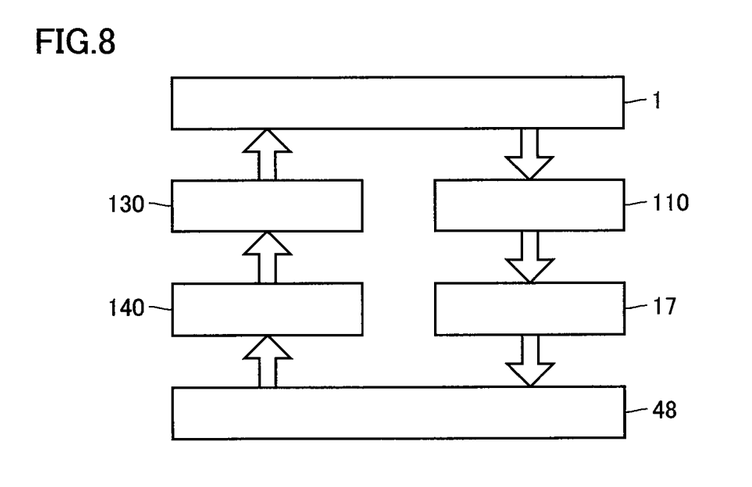
FIG. 8 is a schematic diagram for illustrating feedback control in the linear body insertion device including the operation portion shown in FIG. 7.

As shown in FIG. 8, as an operator 48 operates operation portion 140, drive portion 130 which will be described later controls movement of linear body 1 such as moving forward or backward, based on the output from operation portion 140. In accordance with such movement of linear body 1, when compressive force is applied to linear body 1, sensor portion 110 detects the compressive force. The compressive force detected by sensor portion 110 is transmitted to operator 48 through a tactile sense feedback portion 17. Specifically, motor 47, decelerator 46 and lever 40 shown in FIG. 7 correspond to tactile sense feedback portion 17. As operator 48 operates operation portion 140 in accordance with the information from tactile sense feedback portion 17 (specifically, torque transmitted from motor 47 through decelerator 46 to lever 40), drive portion 130 which will be described later again controls such movement of linear body 1 as moving forward or backward, based on the output from operation portion 140. In accordance with such movement of linear body 1, when compressive force is applied to linear body 1, sensor portion 110 again detects the compressive force applied to linear body 1 as described above. Thus, feedback of the compressive force applied to linear body 1 is provided to operator 48 through sensor portion 110, so that linear body 1 can more accurately and reliably be operated.

The drive portion of the linear body insertion device according to the present invention will be described with reference to FIG. 9.

Figure 9:
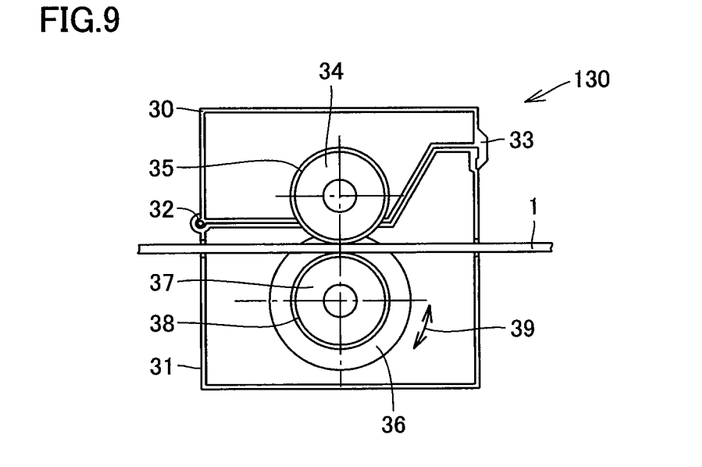
FIG. 9 is a cross-sectional schematic diagram showing a drive portion of the linear body insertion device according to the present invention.

As shown in FIG. 9, drive portion 130 includes an upper housing 30 and a lower housing 31 pivotably connected to each other through a hinge 32, a motor 36 arranged in the housing consisting of upper housing 30 and lower housing 31, a roller 37 connected to a rotation shaft of motor 36, and another roller 34 arranged to be opposed to roller 37. An outer circumferential portion of roller 37 connected to the rotation shaft of motor 36 is coated with rubber 38 serving as an elastic body. As motor 36 revolves, roller 37 can rotate in a direction shown with an arrow 39. Roller 34 is provided at a position opposed to a side surface of roller 37.

An outer circumferential surface of roller 34 is also coated with rubber 35 serving as an elastic body. Rollers 37 and 34 are arranged such that rotation shafts of roller 34 and roller 37 are parallel to each other. Linear body 1 is arranged such that it passes through the housing of drive portion 130 while it is held between the respective outer circumferential surfaces of rollers 37 and 34. Roller 34 is rotatably fixed to upper housing 30. Motor 36 and roller 37 are fixed to lower housing 31. Accordingly, as upper housing 30 pivots around hinge 32 relative to lower housing 31, upper housing 30 and lower housing 31 are opened. Then, linear body 1 is inserted in a through hole formed in lower housing 31 and linear body 1 is provided such that a part of linear body 1 is arranged on the side surface of roller 37. In this state, upper housing 30 pivots around hinge 32 and upper housing 30 and lower housing 31 are connected and fixed to each other by means of a locking portion 33. Consequently, linear body 1 is held between rollers 34 and 37. Then, as motor 36 revolves in the direction shown with arrow 39 in accordance with the operation of operation portion 140 described above, roller 37 rotates to be able to move linear body 1 forward or backward. Here, operation portion 140 and drive portion 130 are connected to each other through a wire or the like so that a control signal from operation portion 140 can be transmitted to drive portion 130.

It is noted that rubber 35, 38 with which the outer circumferential surface of roller 34 and 37 is coated may be replaced with another material, so long as linear body 1 can be held without slipping. For example, instead of rubber 35, 38, a soft material such as other resins may be employed.

Variations of the linear body insertion device according to the present invention will be described with reference to FIGS. 10 and 11.

Figure 10:
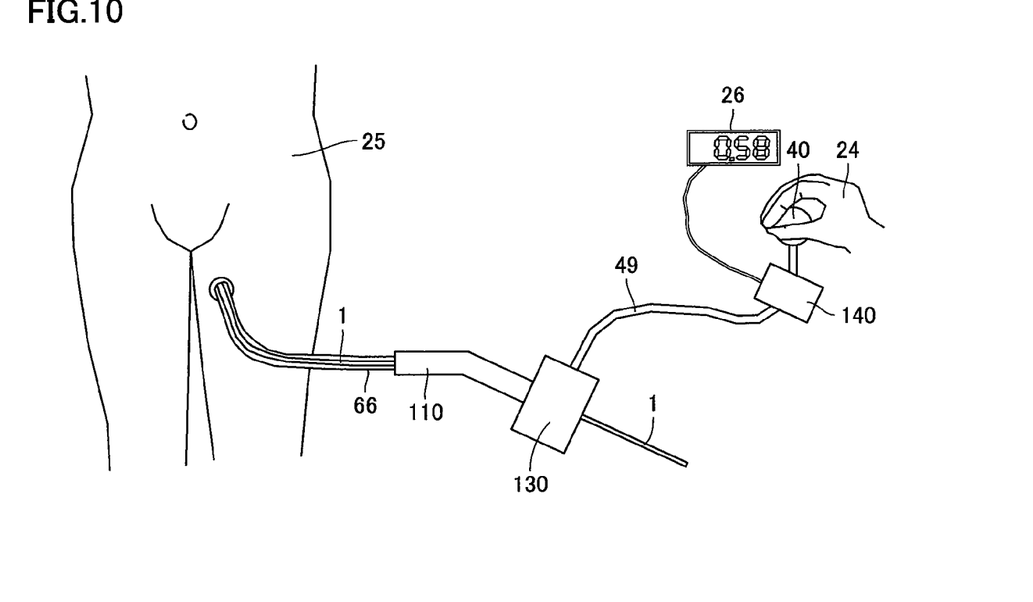
FIG. 10 is a schematic diagram showing a variation of the linear body insertion device according to the present invention shown in FIGS. 1 and 2.

Though the linear body insertion device shown in FIG. 10 has the structure basically similar to that of the linear body insertion device shown in FIGS. 1 and 2, it is different in that drive portion 130 and operation portion 140 are connected to each other through a connection wire 49 and drive portion 130 and operation portion 140 are arranged at a distance from each other. Here, for example, in arranging an embolic coil in an aneurysm (such as a cerebral aneurysm) in a human body using linear body 1, such an operation is performed under X-ray fluoroscopy of a site to be filled with the coil. Namely, the operator operating linear body 1 operates the linear body insertion device around an X-ray apparatus. Consequently, the operator is exposed to the X-rays, although exposure may be little. Therefore, in order to reduce an amount of exposure of the operator, the operator preferably performs the operation at a position distant from the X-ray fluoroscopy apparatus. Accordingly, operation portion 140 is physically separated from drive portion 130 and operation portion 140 and drive portion 130 are connected to each other through connection wire 49, so that the operator can perform what is called remote operation at a position distant from a human body under surgical operation. Connection between operation portion 140 and drive portion 130 may be achieved by electrical connection through connection wire 49 as illustrated, however, optical connection through an optical fiber or wireless connection through infrared or other electromagnetic waves may be employed. Alternatively, in order to enable remote operation at a further distant position, connection between drive portion 130 and operation portion 140 may be achieved through a public line such as a telephone line or other network circuits such as the Internet.

Figure 11:
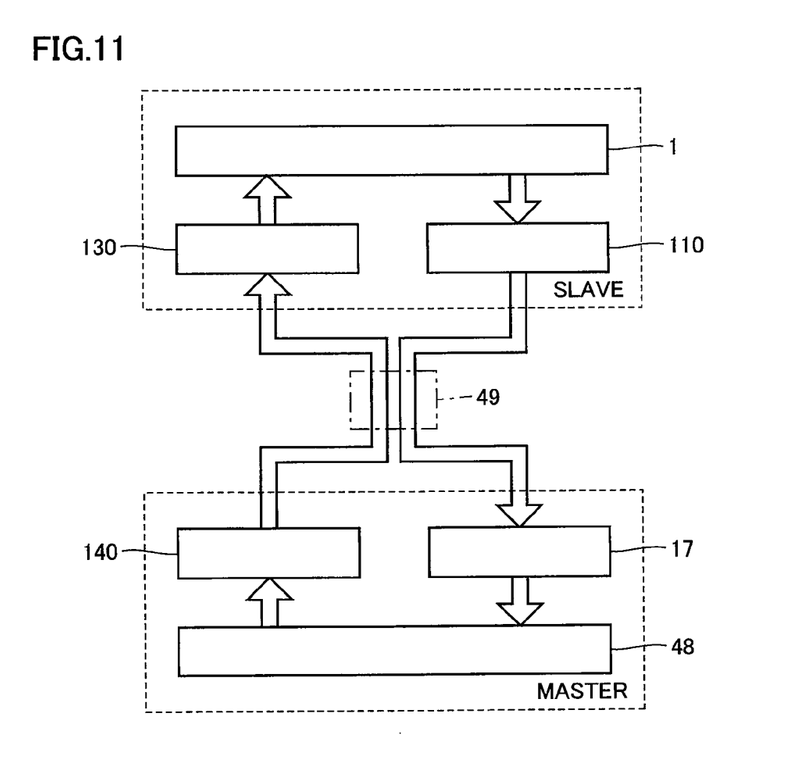
FIG. 11 is a schematic diagram for illustrating feedback control in the linear body insertion device shown in FIG. 10.

As shown in FIG. 11, feedback control in the linear body insertion device shown in FIG. 10 can be carried out basically as in the linear body insertion device shown in FIGS. 1 and 2. Though the block diagram showing feedback control shown in FIG. 11 is basically similar to the block diagram shown in FIG. 8, the block diagram in FIG. 11 is different in that a transmission path of a signal transmitted from operation portion 140 to drive portion 130 and a signal transmitted from sensor portion 110 to tactile sense feedback portion 17 is implemented in part by connection wire 49. By thus interposing connection wire 49, a position where sensor portion 110 and drive portion 130 are arranged can be distant from a position where operation portion 140 is arranged.

A second variation of the linear body insertion device according to the present invention will be described with reference to FIG. 12.

Figure 12:
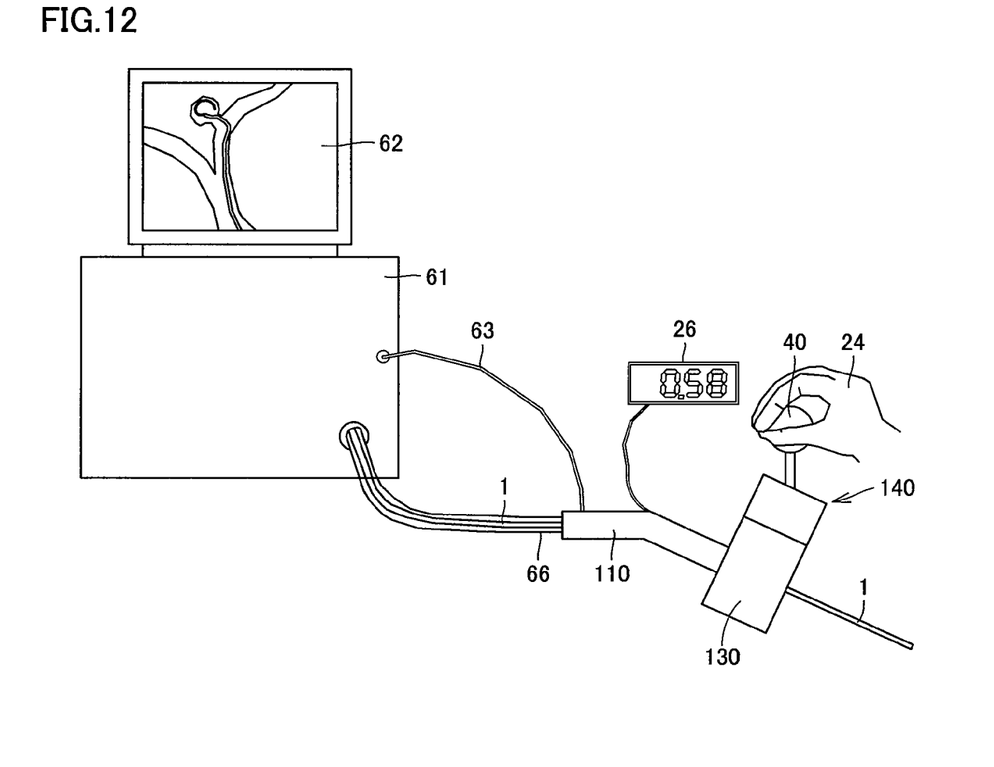
FIG. 12 is a schematic diagram for illustrating a second variation of the linear body insertion device according to the present invention.

As shown in FIG. 12, though the second variation of the linear body insertion device according to the present invention has the structure basically similar to that of the linear body insertion device shown in FIGS. 1 and 2, it is different in that this linear body insertion device is used as a part of an apparatus for training for surgical operations. Namely, as shown in FIG. 12, linear body 1 is connected to a simulator 61 together with catheter 66, through drive portion 130 and sensor portion 110. Simulator 61 is provided with an output device for displaying a simulated perspective image 62. In addition, a main body of simulator 61 and sensor portion 110 are connected to each other through a cable 63.

According to such a structure, operator 24 under training can check simulated perspective image 62 displayed on the output device and a value of compressive force applied to linear body 1 displayed on visualizing instrument 26, while operating lever 40.

A third variation of the linear body insertion device according to the present invention will be described with reference to FIG. 13.

Figure 13:
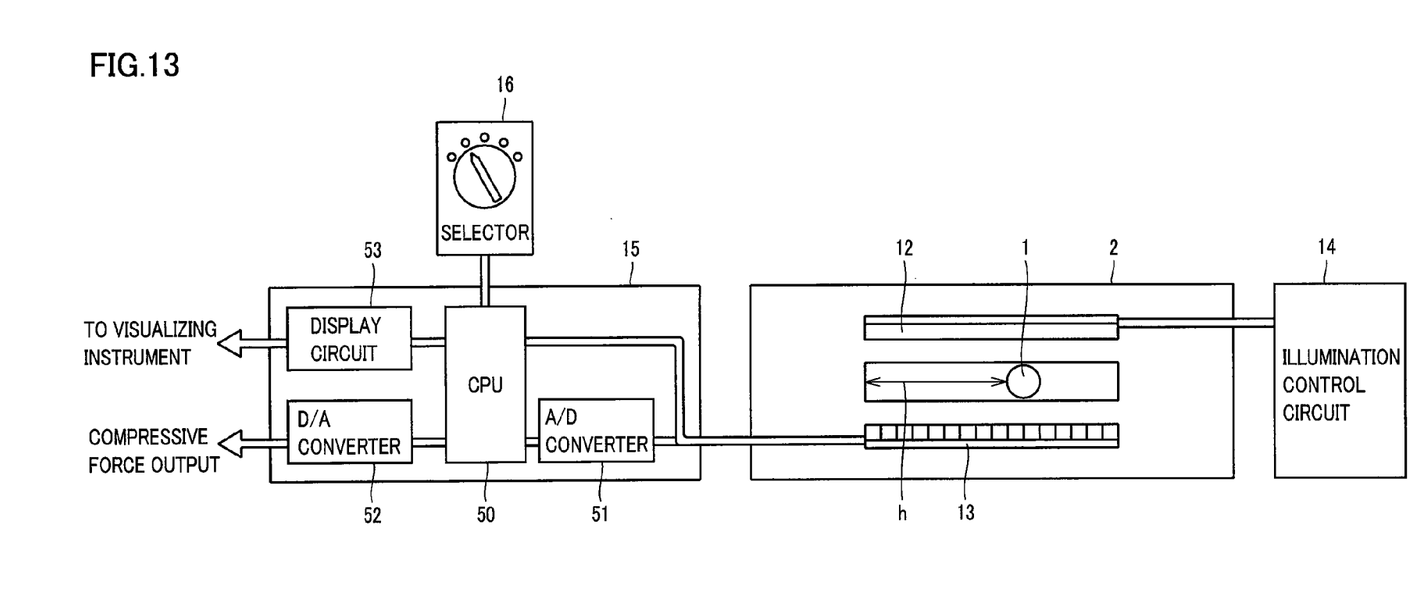
FIG. 13 is a schematic diagram for illustrating a third variation of the linear body insertion device according to the present invention.

FIG. 13 shows sensor portion 110 and processing portion 120 of the linear body insertion device. It is noted that sensor portion 110 in FIG. 13 shows a cross-section in a direction perpendicular to the direction of extension of the through hole and corresponds to FIG. 4. Sensor portion 110 includes, as a line sensor, a linear light source 12 (such as an infrared LED) emitting light and a linear light receiver 13 (such as an optical line sensor implemented by one-dimensionally aligned phototransistors or photodiodes) arranged at a position opposed to linear light source 12 within space 10 and receiving light emitted from linear light source 12. Namely, light source 12 and linear light receiver 13 are arranged across space 10 with linear body 1 lying therebetween, and they are arranged along a direction intersecting the direction of longitudinal axis of linear body 1 and in the direction the same as the direction of bending of linear body 1 when compressive force in the direction of longitudinal axis is applied to linear body 1. In addition, an illumination control circuit 14 for causing linear light source 12 to illuminate is connected to linear light source 12. When linear light receiver 13 receives light emitted from linear light source 12, linear body 1 is located over a certain light-receiving element among the one-dimensionally aligned light-receiving elements and it cuts off light emitted from linear light source 12. Then, a quantity of light received by that light-receiving element decreases. Sensor portion 110 detects a position of linear body 1 (that is, height h of peak of bending of linear body 1 (degree of bending)), based on the position of the light-receiving element at which quantity of light received by linear light receiver 13 is small. Processing portion 120 includes a conversion circuit 15 for converting data of detected degree of bending into compressive force in the direction of longitudinal axis applied to linear body 1. In measurement device main body 2, an optical path from linear light source 12 to linear light receiver 13 is formed of a material through which light used for detection passes.

By detecting the position of the light-receiving element at which quantity of light emitted from linear light source 12 is small, a position of intersection of line sensor 11 and linear body 1 can be detected. Namely, height h of the peak of bending of linear body 1 (degree of bending) can be detected as described above, based on this position of intersection. Then, predetermined correlation between the degree of bending of linear body 1 and compressive force applied to linear body 1 is input to conversion circuit 15. By converting the degree of bending of linear body 1 into compressive force applied to linear body 1 in conversion circuit 15, compressive force applied to linear body 1 can be measured. In order to properly form an image of linear body 1 over linear light receiver 13, an optical element such as a lens, a slit or a filter cutting off outside light may be provided in the present optical system.

Conversion circuit 15 includes an A/D converter (analog/digital converter) 51, a CPU 50 connected to A/D converter 51, a display circuit 53 and a D/A converter (digital/analog converter) 52 receiving an output from CPU 50, and a selector 16 connected to CPU 50. Display circuit 53 is connected to the visualizing instrument. D/A converter 52 is connected, for example, to auralizing instrument 28 or a control circuit for controlling motor 47 shown in FIG. 7, in order to output data of compressive force.

When a plurality of linear bodies 1 different in material are used, correlation between the degree of bending of each of used linear bodies 1 and compressive force in the direction of longitudinal axis applied to linear body 1 is determined in advance and the correlation should be stored in conversion circuit 15. Processing portion 120 includes selector 16 shown in FIG. 13. Accordingly, by selecting which correlation is to be used in accordance with used linear body 1 through selector 16, the same linear body insertion device can be applied to linear bodies 1 made of various materials (that is, having Young's moduli).

A fourth variation of the linear body insertion device according to the present invention will be described with reference to FIGS. 14 to 16. It is noted that FIG. 14 shows a cross-section of sensor portion 110 in the fourth variation of the linear body insertion device according to the present invention.

Figure 14:
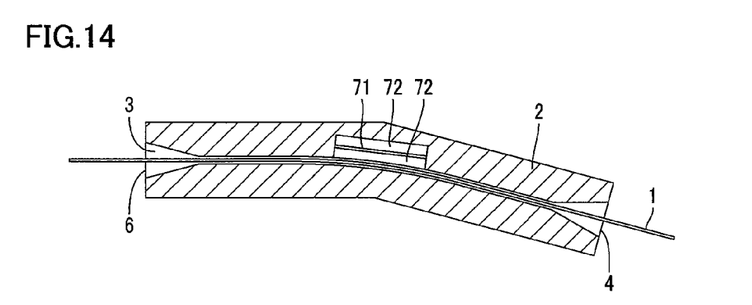
FIG. 14 is a cross-sectional schematic diagram for illustrating a fourth variation of the linear body insertion device according to the present invention.

FIG. 14 shows an internal structure of measurement device main body 2. In addition, FIG. 15 shows a state of linear body 1 within sensor portion 110 when compressive force in the direction of longitudinal axis is applied to linear body 1. In FIG. 14, as in sensor portion 110 shown in FIG. 3 or the like, in order to facilitate insertion by making greater the inlet and the outlet where linear body 1 passes, through hole 3 has tapered input and output ports formed at inlet port 4 and outlet port 6, respectively. In measurement device main body 2, a diameter of through hole 3 is slightly greater than a diameter of linear body 1 (for example, 105% to 120% of the diameter of linear body 1). Therefore, movement of linear body 1 in measurement device main body 2 in a direction other than the direction of longitudinal axis is restricted. It is noted that, at the input and output ports, the height of through hole 3 in a direction perpendicular to the sheet surface is slightly greater than the diameter of linear body 1 (for example, 105% to 120% of the diameter of linear body 1), so that movement of linear body 1 in the direction perpendicular to the sheet surface is restricted. In other words, at the input and output ports, through hole 3 has a rectangular cross-sectional shape at a cross-section perpendicular to the direction of longitudinal axis of linear body 1.

Measurement device main body 2 defines a site on the inner wall of through hole 3 pressed by linear body 1 when compressive force in the direction of longitudinal axis is applied to linear body 1. Namely, through hole 3 includes, within measurement device main body 2, a portion formed in a bent shape with a bending portion of measurement device main body 2 being the peak. Linear body 1 passes through the portion of through hole 3 formed in the bent shape, while it is curving. A strain sensor 71 is arranged between two elastic bodies 72 on an outer side of the portion of the inner wall of through hole 3 formed in the bent shape (an outer circumferential side of the portion formed in the bent shape). Strain sensor 71 is held in a manner sandwiched by elastic bodies 72. As strain sensor 71 is held by elastic bodies 72, when compressive force in the direction of longitudinal axis is applied to linear body 1 and thereafter compressive force is removed, elastic bodies 72 return to the original shape and hence an amount of strain sensed by strain sensor 71 also returns to an original value. Therefore, even when the inner wall of through hole 3 is repeatedly pressed by linear body 1, the amount of strain in accordance with acting force can accurately be sensed by strain sensor 71. It is noted that a strain gauge made of metal or silicon, capable of sensing an amount of strain based on variation of electrical resistance, may be used as strain sensor 71.

Figure 15:
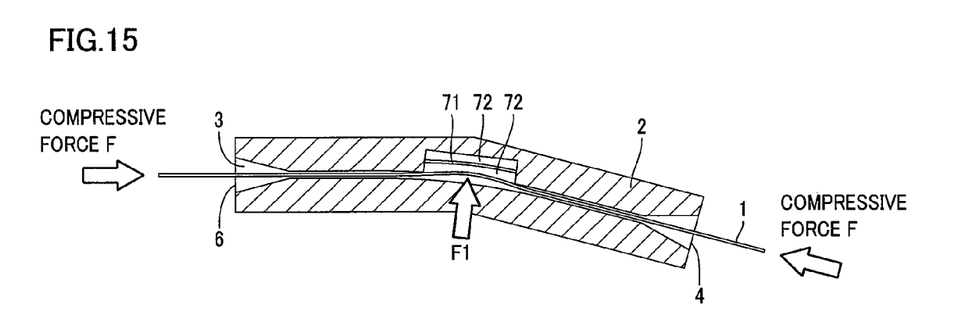
FIG. 15 is a cross-sectional schematic diagram for illustrating an operation of the sensor portion shown in FIG. 14.
Figure 16:
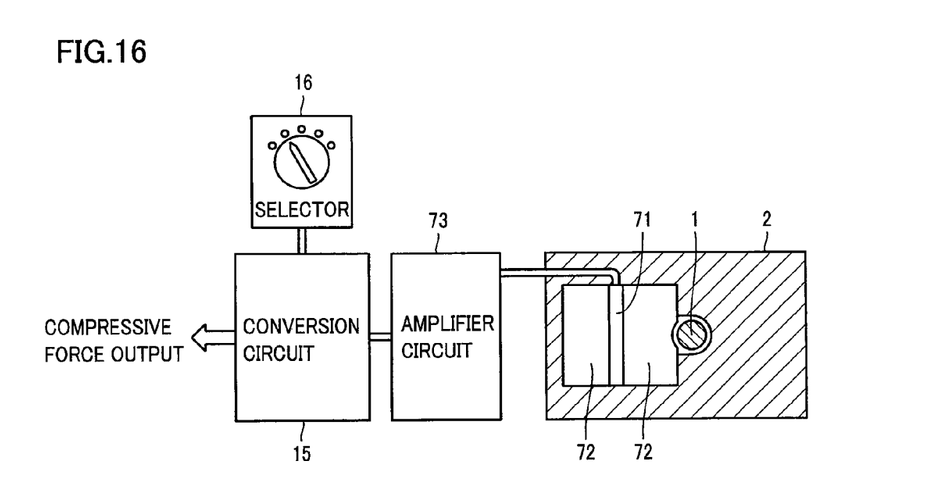
FIG. 16 is a schematic diagram showing the sensor portion and a processing portion in the fourth variation of the linear body insertion device according to the present invention.

When compressive force F in the direction of longitudinal axis is applied to linear body 1 as shown in FIG. 15, or even when small compressive force in the direction of longitudinal axis is applied to linear body 1, linear body 1 tends to bend within through hole 3, because the diameter of through hole 3 is slightly greater than the diameter of linear body 1 and linear body 1 passes through through hole 3 while it is curving. After linear body 1 comes in contact with the outer side of the portion of the inner wall of through hole 3 formed in the bent shape, linear body 1 presses the inner wall. In other words, when compressive force F in the direction of longitudinal axis is applied to linear body 1, force of bending of linear body 1 within through hole 3 serves as acting force F1, linear body 1 presses elastic body 72 between through hole 3 and strain sensor 71, and elastic body 72 undergoes elastic deformation. Elastic deformation of elastic body 72 causes strain and strain sensor 71 senses an amount of the strain. By sensing the amount of strain, acting force F1 with which linear body 1 presses the outer side of the portion of the inner wall of through hole 3 formed in the bent shape can reliably be detected. Detected acting force F1 is converted to compressive force F in the direction of longitudinal axis applied to linear body 1, based on predetermined correlation between acting force F1 and compressive force F applied to linear body 1. Compressive force F in the direction of longitudinal axis applied to linear body 1 can thus reliably be measured and presence of an obstacle within a vessel can be sensed based on increase in compressive force F applied to linear body 1.

If through hole 3 is in a straight shape without including a portion formed in a bent shape, linear body 1 is in a straight shape when it passes through the through hole and linear body 1 is not bent. Even when compressive force in the direction of longitudinal axis is applied to linear body 1, linear body 1 does not deform in a direction other the direction of longitudinal axis until it is buckled. Therefore, compressive force less than buckling load cannot be measured. Therefore, through hole 3 preferably includes a portion formed in a bent shape.

Thus, as the linear body insertion device for operating linear body 1 located outside the vessel in which linear body 1 is to be inserted is provided with sensor portion 110 including measurement device main body 2 so as to measure compressive force in the direction of longitudinal axis applied to linear body 1, an operation for inserting linear body 1 can be performed while quantitatively measuring compressive force in the direction of longitudinal axis applied to linear body 1 also in extremely thin linear body 1 where it is difficult to provide a pressure sensor at the tip end. In FIG. 15, elastic body 72 is arranged between through hole 3 and strain sensor 71 and linear body 1 presses elastic body 72 when compressive force F in the direction of longitudinal axis is applied to linear body 1, however, for example, a material such as metal, that is hardly deformed by acting force F1 (such as a material harder than elastic body 72), may be arranged at a site on the inner wall of through hole 3 pressed by linear body 1. Alternatively, strain sensor 71 may directly be exposed at the inner wall of through hole 3, so that strain sensor 71 comes in contact with linear body 1. Alternatively, an elastic body may be arranged only behind strain sensor 71 when viewed from through hole 3.

A specific operation of sensor portion 110 and processing portion 120 will be described with reference to FIG. 16. In FIG. 16, processing portion 120 includes an amplifier circuit 73 connected to strain sensor 71 of measurement device main body 2, for amplifying an output from strain sensor 71, conversion circuit 15, and selector 16. Conversion circuit 15 converts acting force with which linear body 1 presses the outer side of the portion of the inner wall of through hole 3 formed in the bent shape, that is detected based on the amount of strain sensed by strain sensor 71, into compressive force in the direction of longitudinal axis applied to linear body 1. Selector 16 is similar to selector 16 shown in FIG. 13. Namely, when a plurality of linear bodies 1 different in material are used, correlation between the degree of bending of each of used linear bodies 1 and compressive force in the direction of longitudinal axis applied to linear body 1 is determined in advance and the correlation is stored in conversion circuit 15. By selecting which correlation is to be used in accordance with used linear body 1 through selector 16, the same linear body insertion device can be applied to linear bodies 1 made of various materials (that is, having Young's moduli), as in the linear body insertion device shown in FIG. 13.

A fifth variation of the linear body insertion device according to the present invention will be described with reference to FIGS. 17 and 18.

Figure 17:
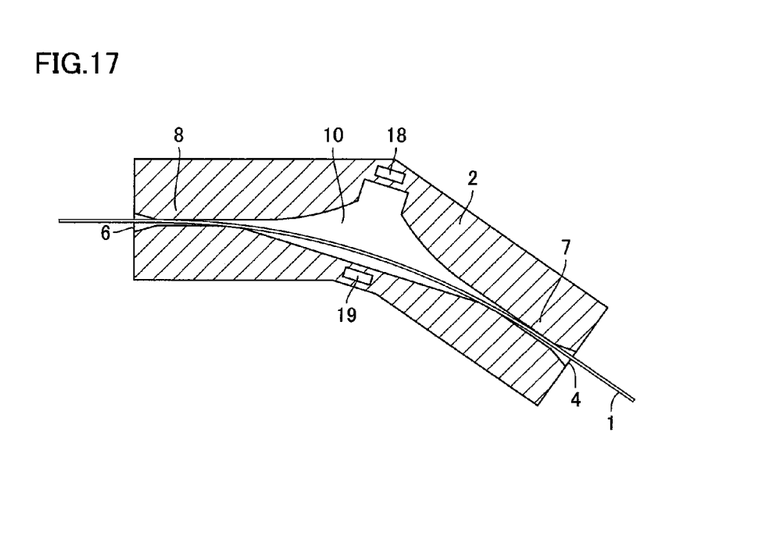
FIG. 17 is a cross-sectional schematic diagram of the sensor portion for illustrating the fourth variation of the linear body insertion device according to the present invention.

As shown in FIG. 17, though sensor portion 110 has a structure basically similar to that of the sensor portion shown in FIG. 3, a type and arrangement of a sensor for detecting information on bending of linear body 1 are different. Specifically, sensor portion 110 shown in FIG. 17 is provided with a light source 18 and a light receiver 19 opposed to each other across space 10 in through hole 3. As shown in FIG. 18, light source 18 and light receiver 19 are arranged such that they are opposed to each other along the direction of movement of linear body 1 when linear body 1 is bent in space 10.

Figure 18:
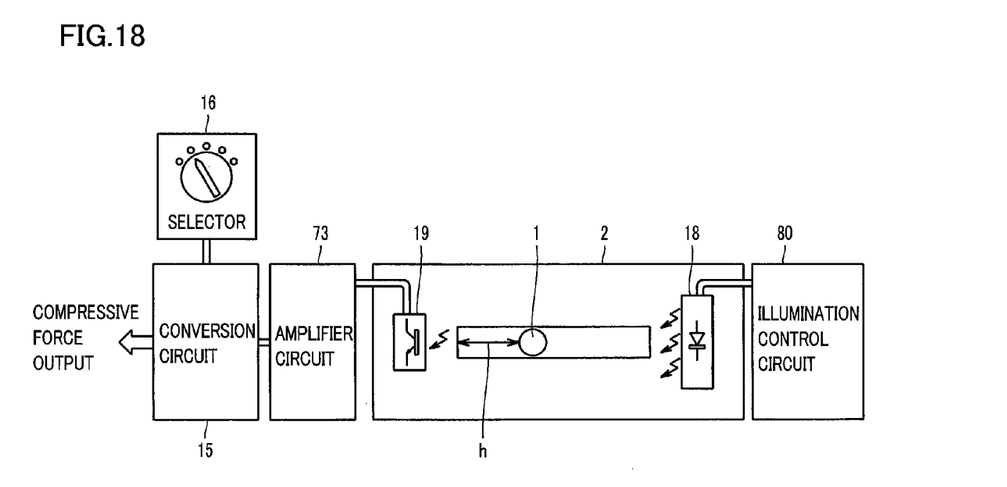
FIG. 18 is a schematic diagram showing the sensor portion and the processing portion in a fifth variation of the linear body insertion device according to the present invention.

As shown in FIGS. 17 and 18, when compressive force in the direction of longitudinal axis is applied to linear body 1, linear body 1 is bent in a prescribed direction in space 10 within through hole 3, that is, toward a wall along which linear body 1 does not extend in space 10. As linear body 1 is bent, height h of the peak of bending, that is, a distance from a wall surface along which linear body 1 extends to linear body 1 increases. Measurement device main body 2 includes an optical sensor in the direction of height of the peak of bending, which detects the degree of bending of linear body 1. The sensor portion includes light source 18 for emitting light (such as an infrared LED) and light receiver 19 (such as a phototransistor) arranged at a position opposed to light source 18 in space 10, for receiving light emitted from light source 18. As shown in FIG. 18, light source 18 and light receiver 19 are arranged to be opposed to each other with linear body 1 lying therebetween, in the longitudinal direction in the rectangular cross-section of through hole 3. When h is small, linear body 1 is located in the vicinity of light receiver 19 and linear body 1 casts large shadow, so that a quantity of light received by light receiver 19 is small. When compressive force is applied to linear body 1 and linear body 1 is bent and when h becomes greater, linear body 1 moves away from light receiver 19 and the quantity of light received by light receiver 19 increases. Therefore, based on the quantity of light received by light receiver 19 with respect to the quantity of light emitted from light source 18, height h of the peak of bending of linear body 1, that is, the degree of bending of linear body 1, can be detected.

In FIG. 18, in sensor portion 110, an illumination control circuit 80 for causing light source 18 to illuminate is connected to light source 18. Processing portion 120 includes amplifier circuit 73 for amplifying an output of light receiver 19, conversion circuit 15 for converting the degree of bending of linear body 1 detected based on the quantity of light received by light receiver 19 with respect to the quantity of light emitted from light source 18 into the compressive force in the direction of longitudinal axis applied to linear body 1, and selector 16. Selector 16 is similar to selector 16 shown in FIG. 13. Namely, when a plurality of linear bodies 1 different in material are used, correlation between the degree of bending of each of used linear bodies 1 and compressive force in the direction of longitudinal axis applied to linear body 1 is determined in advance and the correlation is stored in conversion circuit 15. By selecting which correlation is to be used in accordance with used linear body 1 through selector 16, the same linear body insertion device can be applied to linear bodies 1 made of various materials (that is, having Young's moduli), as in the linear body insertion device shown in FIG. 13. In measurement device main body 2, an optical path from light source 18 to light receiver 19 is formed of a material through which light used for detection passes.

Characteristic features of the present invention will be listed hereinafter, although they may partially be redundant as seen in the embodiments described above.

The linear body insertion device serving as the linear body drive device according to the present invention includes drive portion 130, operation portion 140, sensor portion 110 and processing portion 120 serving as the measurement portion, and output portion 150 serving as the notification portion. Drive portion 130 drives flexible linear body 1. Operation portion 140 includes an input member (operation lever 40) operated by the operator for controlling performance of drive portion 130. Sensor portion 110 included in the measurement portion detects compressive force in the direction of longitudinal axis applied to linear body 1, based on the degree of bending of linear body 1 driven by drive portion 130. Output portion 150 provides notification of data of compressive force detected by the measurement portion. Thus, the compressive force in the direction of longitudinal axis applied to linear body 1 can accurately be detected based on the degree of bending of linear body 1, so that the operator can operate operation portion 140 based on the data of the compressive force provided by output portion 150. Consequently, the operator can safely and reliably operate linear body 1.

In the linear body insertion device above, the measurement portion includes the main body (measurement device main body 2), the sensor (line sensor 11, linear light source 12, linear light receiver 13, light source 18, light receiver 19, strain sensor 71), and processing portion 120 serving as the conversion portion. In measurement device main body 2, through hole 3 through which linear body 1 passes is formed. When compressive force is applied to linear body 1, linear body 1 is bent in a prescribed direction within through hole 3.

The sensor detects the degree of bending. Processing portion 120 converts the detected degree of bending into compressive force applied to linear body 1. Here, when the tip end of linear body 1 comes in contact with an obstacle and compressive force in the direction of longitudinal axis is applied to linear body 1, sensor portion 110 can detect the degree of bending of linear body 1. Then, the detected degree of bending of linear body 1 can be converted to compressive force in the direction of longitudinal axis applied to linear body 1, for example, based on predetermined correlation between the degree of bending of linear body 1 and compressive force applied to linear body 1. Thus, presence of an obstacle in a direction of travel of linear body 1 can be sensed based on increase in compressive force. In addition, as the linear body insertion device according to the present invention is not much restricted in terms of a material or the like for linear body 1 to be used, it is applicable to linear bodies 1 of various shapes or materials. Consequently, linear body 1 as used so far can be used with the linear body drive device according to the present invention without modification, which leads to cost effectiveness.

In the linear body insertion device above, drive portion 130 includes a pair of rollers 34, 37 sandwiching linear body 1 and motor 36 serving as the drive member. Motor 36 rotatably drives at least one of the pair of rollers 34 and 37. Here, drive portion 130 can be implemented by relatively simple devices of motor 36 and rollers 34 and 37 as combined.

In the linear body insertion device above, operation portion 140 and drive portion 130 may mechanically be separated from each other. The device for driving linear body 1 above may further include a connection member (connection wire 49) for electrically connecting separated operation portion 140 and drive portion 130 to each other. Thus, only operation portion 140 can be arranged at a position distant from drive portion 130 (which is provided around the patient), so that the operator can operate the linear body insertion device at a position distant from the patient.

In the linear body insertion device above, a connection member may be a wire for electrically connecting drive portion 130 and operation portion 140 to each other, an optical fiber for transmitting an optical signal, or a transmitter and a receiver provided in each of drive portion 130 and operation portion 140, capable of transmitting and receiving a signal through an electromagnetic wave (light, infrared, or other electromagnetic waves) between drive portion 130 and operation portion 140.

In the linear body insertion device above, operation portion 140 may have at least any one of operation lever 40, a pedal, and a dial, as the input member. Here, the operation portion can be implemented as a relatively simple structure.

In the linear body insertion device above, output portion 150 includes at least any one of visualizing instrument 26, 27 for displaying data and auralizing instrument 28 for converting the data into voice and sound for output. Here, visualizing instrument 26, 27 and auralizing instrument 28 can quantify and display kinesthetic sense of the operator. In addition, such data may also be recorded, for example, in an external recording device. Therefore, manipulation of a skilled operator can quantitatively be transferred to a less experienced operator. Moreover, the operator can reliably recognize the time when compressive force applied to linear body 1 is equal to or greater than a predetermined threshold value.

In the linear body insertion device above, processing portion 120 included in the measurement portion may output a signal in accordance with the data of the compressive force to operation portion 140. Operation portion 140 may include a feedback output member (motor 47) for varying an operation resistance of the input member (operation lever 40) in accordance with the signal. Here, the compressive force applied to linear body 1 can be transmitted to the operator as tactile sense, depending on magnitude of resistance in operation of operation lever 40 of operation portion 140 by the operator (magnitude of force necessary for moving operation lever 40).

In the linear body insertion device above, a linear body for medical use may be employed as linear body 1. Here, as the linear body insertion device according to the present invention can be used in a surgical operation or the like using linear body 1 for medical use, linear body 1 can safely and reliably be operated while the data of compressive force applied to linear body 1 is quantitatively grasped. Therefore, safety and accuracy of the surgical operation using linear body 1 can be improved.

The linear body insertion device may be provided in medical simulator 61 simulating a human body as shown in FIG. 12. Here, manipulation of a skilled operator can be quantified and quantitative transfer of manipulation to a less experienced operator can be promoted. Therefore, manipulation of the less experienced operator can quickly be improved.

It should be understood that the embodiments disclosed herein are illustrative and non-restrictive in every respect. The scope of the present invention is defined by the terms of the claims, rather than the description above, and is intended to include any modifications within the scope and meaning equivalent to the terms of the claims.

The invention claimed is:

1. A linear body drive device, comprising:
   a drive portion for driving a linear body having flexibility;
   an operation portion including an input member operated by an operator for controlling performance of said drive portion;
   a measurement portion for detecting compressive force in a direction of longitudinal axis applied to said linear body, based on a degree of bending of said linear body driven by said drive portion; and
   a notification portion for providing notification of data of said compressive force detected by said measurement portion, wherein said measurement portion includes:
      a main body in which a through hole through which said linear body passes is formed, said linear body being bent in a prescribed direction within said through hole when said compressive force is applied to said linear body,
      a sensor for detecting said degree of bending, and
      a conversion portion for converting detected said degree of bending into said compressive force applied to said linear body.

2. The linear body drive device according to claim 1, wherein
   said drive portion includes
   a pair of rollers sandwiching said linear body, and
   a drive member for rotatably driving at least one of said pair of rollers.

3. The linear body drive device according to claim 1, wherein
   said operation portion and said drive portion can mechanically be separated from each other, and
   said linear body drive device further comprises a connection member for electrically connecting separated said operation portion and said drive portion to each other.

4. The linear body drive device according to claim 1, wherein
   said operation portion has at least any one of a lever, a pedal, and a dial, as said input member.

5. The linear body drive device according to claim 1, wherein
   said notification portion includes at least any one of a visualizing instrument for displaying said data and an auralizing instrument for converting said data into voice and sound for output.

6. The linear body drive device according to claim 1, wherein
   said measurement portion outputs a signal in accordance with the data of said compressive force to said operation portion, and
   said operation portion includes a feedback output member for varying an operation resistance of said input member in accordance with said signal.

7. The linear body drive device according to claim 1, wherein
   a linear body for medical use is employed as said linear body.

8. The linear body drive device according to claim 7, provided in a medical simulator simulating a human body.

* * * * *